(12) United States Patent
Payton et al.

(10) Patent No.: US 8,483,816 B1
(45) Date of Patent: Jul. 9, 2013

(54) SYSTEMS, METHODS, AND APPARATUS FOR NEURO-ROBOTIC TRACKING POINT SELECTION

(75) Inventors: David W. Payton, Calabasas, CA (US); Michael J. Daily, Thousand Oaks, CA (US)

(73) Assignee: HRL Laboratories, LLC, Malibu, CA (US)

( * ) Notice: Subject to any disclaimer, the term of this patent is extended or adjusted under 35 U.S.C. 154(b) by 545 days.

(21) Appl. No.: 12/699,660

(22) Filed: Feb. 3, 2010

(51) Int. Cl.
*A61B 5/04* (2006.01)

(52) U.S. Cl.
USPC .......................................... 600/544; 700/245

(58) Field of Classification Search
USPC ................................. 600/544, 545
See application file for complete search history.

(56) References Cited

U.S. PATENT DOCUMENTS

| | | | |
|---|---|---|---|
| 5,363,858 A | 11/1994 | Farwell | |
| 5,467,777 A | 11/1995 | Farwell | |
| 7,209,788 B2* | 4/2007 | Nicolelis et al. | 607/48 |
| 7,260,430 B2 | 8/2007 | Wu et al. | |
| 7,392,079 B2* | 6/2008 | Donoghue et al. | 600/545 |
| 7,546,158 B2* | 6/2009 | Allison et al. | 600/544 |
| 8,069,125 B2 | 11/2011 | Jung et al. | |
| 2002/0058867 A1 | 5/2002 | Breiter et al. | |
| 2002/0103429 A1 | 8/2002 | deCharms | |
| 2004/0073414 A1* | 4/2004 | Bienenstock et al. | 703/2 |
| 2004/0267320 A1* | 12/2004 | Taylor et al. | 607/2 |
| 2005/0273890 A1* | 12/2005 | Flaherty et al. | 901/50 |
| 2009/0156907 A1 | 6/2009 | Jung et al. | |

OTHER PUBLICATIONS

Bayliss et al., "Changing the P300 Brain Computer Interface," CyberPsychology & Behavior, vol. 7, No. 6, 2004, pp. 694-704.

Jessica D. Bayliss, "Use of the Evoked Potential P3 Component for Control in a Virtual Apartment," IEEE Transactions on Neural Systems and Rehabilitation Engineering, vol. 11, No. 2, Jun. 2003, pp. 113-116.

Berka et al., "Real-Time Analysis of EEG Indexes of Alertness, Cognition, and Memory Acquired With a Wireless EEG Headset," International Journal of Human-Computer Interaction, vol. 17, No. 2, 2004, pp. 151-170.

Berka et al., "EEG Indices Distinguish Spatial and Verbal Working Memory Processing: Implications for Real-Time Monitoring in a Closed-Loop Tactical Tomahawk Weapons Simulation," First International Conference on Augmented Cognition, Jul. 2005, 10 pages.

Berka et al., "EEG quantification of alertness: Methods for early identification of individuals most susceptible to sleep deprivation," Proceedings of the SPIE Defense and Security Symposium, Biomonitoring for Physiological and Cognitive Performance during Military Operations, vol. 5797, 2005, pp. 78-89 (12 pages).

(Continued)

*Primary Examiner* — Navin Natnithithadha
*Assistant Examiner* — Etsub Berhanu
(74) *Attorney, Agent, or Firm* — Hanley, Flight & Zimmerman LLC

(57) ABSTRACT

Systems, methods, and apparatus for neuro-robotic tracking point selection are disclosed. A described example method to control a robot arm includes presenting one or more potential trackable features of a target object, emphasizing at least one of the potential trackable features, determining a selection of one of the emphasized features as a tracking point by monitoring a first mental response to emphasizing the feature, and effectuating an end goal via a robot by tracking the selected feature and effectuating a position based on the selected feature.

14 Claims, 6 Drawing Sheets

OTHER PUBLICATIONS

Berka et al., "Implementation of a Closed-Loop Real-Time EEG-Based Drowsiness Detection System: Effects of Feedback Alarms on Performance in a Driving Simulator," Proceedings of the International Conference on Human Computer Interaction, Jul. 2005, 10 pages.

Cheng et al., "Design and Implementation of a Brain-Computer Interface With High Transfer Rates," IEEE Transactions on Biomedical Engineering, vol. 49, No. 10, Oct. 2002, pp. 1181-1186.

Cichocki et al., "Noninvasive BCIs: Multiway Signal-Processing Array Decompositions," IEEE Computer Society, Oct. 2008, pp. 34-42.

Donchin et al., "The Mental Prothesis: Assessing the Speed of a P300-Based Brain-Computer Interface," IEEE Transactions on Rehabilitation Engineering, vol. 8, No. 2, Jun. 2000, pp. 174-179.

Gerson et al., "Cortically-coupled Computer Vision for Rapid Image Search," IEEE Transactions on Neural Systems and Rehabilitation Engineering, vol. 14, No. 2, Jun. 2006, pp. 174-179.

Lalor et al., "Steady-State VEP-Based Brain-Computer Interface Control in an Immersive 3D Gaming Environment," EURASIP Journal on Applied Signal Processing, 2005, pp. 3156-3164.

David G. Lowe, "Distinctive Image Features from Scale-Invariant Keypoints," International Journal of Computer Vision, Jan. 5, 2004, pp. 91-110.

Martinez et al., "Fully-Online, Multi-Command Brain Computer Interface with Visual Neurofeedback Using SSVEP Paradigm," Laboratory for Advanced Brain Signal Processing, RIKEN Brain Science Institute, 2007, 28 pages.

Schogl et al., "BioSig: A Free and Open Source Software Library for BCI Research," IEEE Computer Society, 2008, pp. 44-50.

Wolpaw et al., "Control of a two-dimensional movement signal by a noninvasive brain-computer interface in humans," PNAS, vol. 101, No. 51, Dec. 21, 2004, pp. 17849-17854.

Jonathan R. Wolpaw, "Brain-computer interfaces as new brain output pathways," The Journal of Physiology, 579, 2007, pp. 613-618.

Bell et al., "Control of a humanoid robot by a noninvasive brain-computer interface in humans," Journal of Neural Engineering, 2008 pp. 214-220.

Jonathan Sherwood, "Give it a Thought—and Make it so," University of Rochester, Brain-Computer Interface and Virtual Reality, May 3, 2000, 2 pages.

Khosla et al., "Spatio-temporal EEG source localization using simulated annealing," IEEE Trans Biomed Eng, 44 (11):1075-1091. 2007 (17 pages).

Khosla et al., "An iterative Bayesian maximum entropy method for the EEG inverse problem," In: EA Hoffman (Ed), Physiology Function from Multidimensional Images. Proc SPIE Medical Imaging, 1997 pp. 147-158.

Khosla et al., "Three-dimensional EEG source imaging via maximum entropy method," In IEEE Nuclear Science Symposium and Medical Imaging Conference Record, 1995, vol. 3: pp. 1515-1519.

Kholsa et al., "Spatial mislocationsation of EEG electrodes—effects on accuracy of dipole estimation," Clin Neurophysiol, 1999, 110(2): pp. 261-271.

Kholsa et al. Bio-inspired visual attention and object recognition, Proc. SPIE 6560, 656003, (2007) 11 pages.

Kholsa et al. A bio-inspired system for spatio-temporal recognition instatic and video imagery Proc. SPIE 6560, 656002, (2007) 8 pages.

Srinivasa et al., "A Self-Organizaing Neural Model for Fault Tolerant Control of Redundant Robots," In Proceedings of the IEEE International Joint Conference on Neural Networks, pp. 483-488, 2007.

Srinivasa et al., "A Bio-Inspired Kinematic Controller for Obstacle Avoidance during reaching tasks with Redundant Robots," to apper in IEEE BioRob2008 confernce, Scottsdale AZ, 8 pages.

McFarland et al., "Electroencephalographic (EEG) Control of Three-Dimensional Movement," In Soc. for Neuroscience Abstract, 2008.

Parra et al., "Recipes for the linear analysis of EEG," NeuroImage 28, 2005, pp. 326-341.

Parra et al., "Adaptive Brain Computer-Interface 1. for Augmented Cognition and Action," http://liinc.bme.columbia.edu/~augcog/, retrieved online Jun. 16, 2010, 3 pages.

United States Patent and Trademarke Office, "Office action", issued Mar. 15, 2012, in connection with U.S. Appl. No. 12/699,679, Mar. 15, 2012, (21 pages).

* cited by examiner

SYSTEMS, METHODS, AND APPARATUS FOR NEURO-ROBOTIC TRACKING POINT SELECTION

FIELD OF THE DISCLOSURE

This disclosure relates generally to brain-controlled human-machine interfaces and, more particularly, to systems, methods, and apparatus for neuro-robotic tracking point selection.

BACKGROUND

In the field of robotic control, current control methods are problem-specific. Thus, a particular task requires specialized robotic control methods, and there are no general solutions that may be applied to many different problem situations and robot configurations. Specialized control methods are often brittle and do not easily adapt to unforeseen circumstances.

Electroencephalograms (EEGs) are often used in brain-based interfaces to decode neural activity within the brain. EEGs are non-invasive and produce rapid responses to stimuli. EEG brain-based control techniques can be divided into two classes: endogenous and exogenous. For endogenous techniques, a subject employs imagination to evoke a particular brain wave pattern, which is measured by the EEG. However, endogenous methods require a long training period for the user to learn to produce distinguishable mental responses.

Exogenous techniques use external stimuli to evoke a desired EEG response. The exogenous techniques require far less user training than endogenous techniques. One particular neural response, the P300 signal, is reliably and robustly detected by the EEG. The P300 signal is a mental response to unpredictable stimuli in an oddball paradigm, such as an expected event occurring at an unexpected time.

BRIEF SUMMARY

Systems, methods, and apparatus for neuro-robotic tracking point selection are described herein. Some example methods to control a robot arm include presenting one or more potential trackable features of a target object, emphasizing at least one of the potential trackable features, determining a selection of one of the emphasized features as a tracking point by monitoring a first mental response to emphasizing the feature, and effecting the end goal at a position based on the selected feature via a robot by tracking the selected feature and.

Some example articles of manufacture are also described, including machine readable instructions which, when executed, cause a machine to present one or more potential trackable features of a target object, emphasize at least one of the potential trackable features, determine a selection of one of the emphasized features as a tracking point by monitoring a first mental response to emphasizing the feature, and effect the end goal at a position based on the selected feature by tracking the selected feature and.

Some additional example methods to control a robot are also described, which include identifying a plurality of potential tracking features on a target object, displaying the potential tracking features and an image of the target object, emphasizing a first one of the features, identifying first mental activity in response to emphasizing the first one of the feature, determining whether the first mental activity corresponds to a selection of the emphasized feature, and establishing a tracking point in response to determining that the emphasized feature was selected. In some examples, the method further includes displaying an offset indicator and a plurality of directional indicators, emphasizing one of the directional indicators corresponding to a first direction, identifying second mental activity in response to emphasizing the directional indicator, determining whether the second mental activity corresponds to a selection of the emphasized directional indicator, moving the offset indicator in the first direction in response to determining the emphasized directional indicator is selected, and effecting the goal based on the selected feature and the offset indicator.

In some examples, monitoring the first mental response includes monitoring an electroencephalogram (EEG) to identify a brain signal, where the brain signal corresponds to the selection of the potential trackable feature, and associating the selected potential trackable feature as the tracking point corresponding to the brain signal. In some examples, the first mental response includes at least one of a P300 signal or a steady-state visual evoked response.

Some example methods further include presenting the target object and the selected feature, presenting an offset indicator and one or more directional indicators, emphasizing at least one of the directional indicators and monitoring the EEG for a second mental response corresponding to a selection of the emphasized directional indicator, and moving the offset indicator in a direction corresponding to a first one of the emphasized directional indicators in response to identifying the second mental response from the EEG as corresponding to a selection of the first emphasized directional indicator. In some examples, emphasizing the potential trackable feature or the directional indicator includes at least one of flashing, blinking or flickering the potential trackable feature or the directional indicator. Some example methods further include generating an image of the target object and analyzing the image to determine the potential trackable features.

Some described example methods further include determining potential trackable features by analyzing a plurality of images of the target object to determine features that are consistently present. In some examples, effecting the end goal includes using a visual-servo controller to track the selected feature and to servo a robot based on the tracking. In some examples, effecting the end goal comprises controlling a robotic grappling task to grapple the target object at the end goal.

Some example robot control systems are also described, which include a feature identifier, a feature an image presenter, a classifier, and a robot interface. In some examples, the feature identifier receives an image of a target object and determines a plurality of potential trackable features on the target object. Some example feature and image presenters are coupled to the feature generator to display the image of the target object, to emphasize one of more of the potential trackable features, to receive a selection of the emphasized feature, and to determine an offset from the selected feature as a goal. In some examples, the classifier classifies a mental response to the one or more emphasized features, and determines that the mental response corresponds to the selection of a first one of the emphasized features. In some examples, the robot interface is coupled to the classifier to generate control information to effectuate control a robot action based on the first emphasized feature corresponding to an identified brain signal.

Some example robot control systems further include a parameter generator coupled to the classifier, to the feature generator, and to the robot controller, to determine which potential trackable feature is emphasized, to receive the mental response from the classifier, and to provide a movement direction to the feature generator. In some examples, the parameter generator provides the selected feature and the offset to the robot controller. In some example systems, the feature generator generates a tracking point, an offset indicator, and one or more directional indicators in response to the selected emphasized feature.

Some described example robot control systems further include a visual-servo controller to cause the robot to move toward the target object based on the first emphasized feature. In some examples, the display displays one or more of the directional indicators, the feature and image presenter emphasizes one of the directional indicators, and the classifier classifies the mental response to the emphasized directional indicator. In some examples, the feature generator generates the offset indicator at a second location consistent with the emphasized directional indicator based on the mental response to the emphasized directional indicator. Some example systems further include an image generator or a camera to provide one or more images of the target object to the feature generator. In some example systems, the mental response comprises at least one of a P300 response or a steady-state visual evoked potential. In some examples, the feature generator analyzes a plurality of images of the target object and determines the plurality of potential trackable features based on features that are consistently present in the plurality of images.

DETAILED DESCRIPTION

Figure 1:
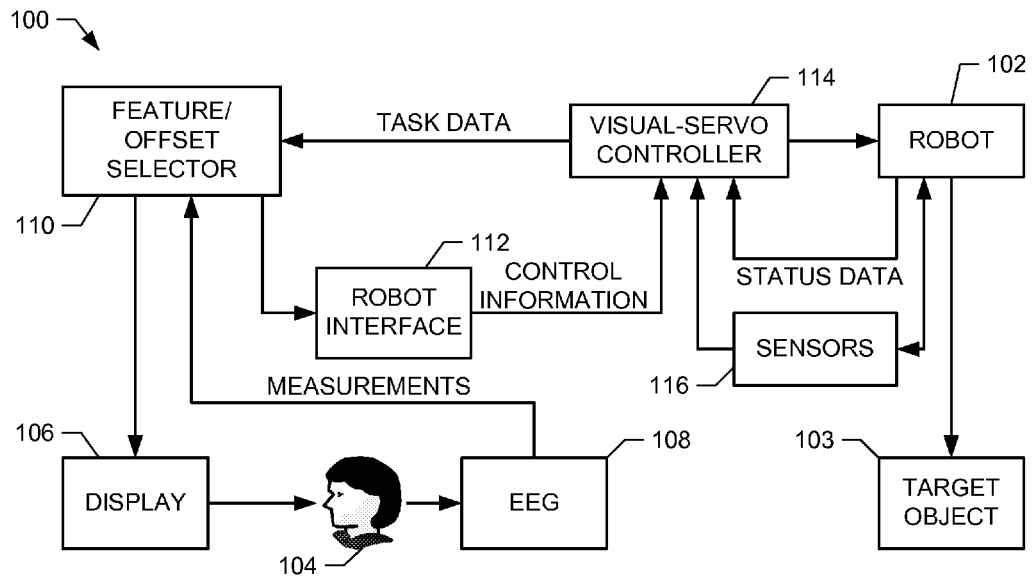
FIG. 1 is a block diagram of an example robot control system.

Certain examples are shown in the above-identified figures and described in detail below. In describing these examples, like or identical reference numbers may be used to identify common or similar elements. The figures are not necessarily to scale and certain features and certain views of the figures may be shown exaggerated in scale or in schematic for clarity and/or conciseness. Although the following discloses example systems, methods, and apparatus, it should be noted that such systems, methods, and apparatus are merely illustrative and should not be considered as limiting. The example circuits described herein may be implemented using discrete components, integrated circuits (ICs), hardware that is programmed with instructions, or any combination thereof. Accordingly, while the following describes example systems, methods, and apparatus, persons of ordinary skill in the art will readily appreciate that the examples are not the only way to implement such systems, methods, and apparatus.

The example systems, methods, and apparatus described herein provide a robust, brain-in-the-loop solution to control robot activities. The example systems, methods, and apparatus incorporate human judgment into a control activity to utilize human experience and problem-solving, which allows a more flexible, yet robust, control solution. In contrast to previous robot control systems, the example systems, methods, and apparatus described below allow input of a computer-trackable feature by the user without using physical controls (e.g., a joystick). Therefore, the example systems, methods, and apparatus may be adapted to many different tasks and many different variations of the tasks. Additionally or alternatively, the tracking feature may be adapted to be as large or small as necessary for a given application. Example applications may include, but are not limited to, space operations, manufacturing, hazardous waste processing and removal, improvised explosive device (IED) disassembly, and prosthetics. Additionally, while the following description includes an example related to robotic arm control, the control techniques and systems described herein are not necessarily limited to such an example implementation.

Some example systems described herein use precise, robot-controlled movements to effect a final goal. However, the visual-servo controller that controls the robot movements uses a defined location or feature that can be visually tracked. If the location or feature moves or is no longer visible, the visual-servo controller loses track of the feature and must start over with a new feature. Untrackable features can often occur in environments where lighting is not constant or when using target objects that have glossy, mirror-like surfaces. For example, a mirror-like surface can present a feature at one location and distance, but the location and/or distance moves when the target object or the camera serving the visual-servo controller moves. To overcome this instability, the example system allows a user to select, via mental responses, a trackable feature that may be used by the visual-servo controller to effect the goal. In this way, the experience and problem-solving ability of the user is utilized to select an appropriate tracking point that a machine may have more difficulty identifying.

An example system analyzes a view of a goal, generated by a camera, to determine potential trackable features. The system then overlays the potential features onto an image of the target object for presentation to the user. The user, employing his or her knowledge and experience, selects one of the trackable features to be tracked by the visual-servo controller. The user concentrates on a particular feature that may be tracked by the visual-servo controller, and an EEG system measures the user's mental responses (e.g., brain signals) while the system emphasizes the features to the user. In some examples, the system emphasizes the features to the user one at a time or more than one at a time. When a classifier, monitoring the EEG system, identifies a particular mental response (e.g., the P300 signal), the emphasized feature is selected and tracked via the visual-servo controller.

Not all potential trackable features will be suitable as an end goal. For example, in a grappling task, an optimal or acceptable grapple point may be offset from a more trackable feature. Thus, once the trackable feature is determined by the user, the system presents a second marker and a directional control to allow the user to position the grappling point at a desired spot. The visual-servo control then grapples the grappling position by tracking the trackable feature and engaging a position offset from the trackable feature. Thus, the user may input a tracking point into the system, which is then used to track the target object in a closed-loop robot control method such as visual-servoing.

FIG. 1 is a block diagram of an example robot control system. The robot control system 100 controls a robot 102 to reach a target object 103. A user 104 interacts with the robot control system 100 by viewing the target object 103 via a display 106 and selecting goals and constraints via an EEG system 108. The display 106 presents an image of the target object 103 and several features to the user 104. Alternatively, the user 104 may view the actual target object 103 directly or through goggles and/or any other presentation device, and the display 106 presents a heads up display (HUD) to overlay the features onto the target object 103. The user 104 uses his or her experience and knowledge to identify one of the features as a goal. As exampled in detail below, while the user 104 identifies and concentrates on a feature, the EEG system 108 measures the user's 104 brain waves which may be used to identify particular mental responses that correspond to a selection of an emphasized feature by the user 104. Thus, when the feature concentrated upon by the user 104 is emphasized by the system 100, the system 100 detects the user's 104 mental responses (e.g., a P300 signal) indicating that the emphasized feature matches the feature on which the user 104 is concentrating.

A feature/offset selector 110 determines the goals and constraints selected by the user 104. As described below, the feature/offset selector 110 receives one or more images of the target object 103. The feature/offset selector 110 presents one of the received images of the target object 103 to the user 104 along with several features that are potentially trackable. The feature/offset selector 110 then emphasizes the potential trackable features until a mental response (e.g., a P300 response) is identified from EEG measurements from the EEG system 108 to identify one of the potential trackable features on which the user 104 was concentrating. After selecting the feature, the feature/offset selector 110 is then presented with an offset indicator, which may be positioned by the user 104 via the EEG system 108 as described in more detail below. Based on the feature and the offset selected by the user 104, the feature/offset selector 110 sends commands to a robot interface 112.

The feature/offset selector 110 elicits a precise goal from the user 104 by selecting a feature that may be used for tracking the target object 103 and specifying an offset from the tracked feature. When the feature/offset selector 110 has established the precise goal, the feature/offset selector 110 may provide commands and parameters for the robot 102 to fully effect the goal. The commands and parameters from the feature/offset selector 110 are translated by the robot interface 112. The translated commands and/or parameters may differ widely between different robot applications. The feature/offset selector 110 is described in more detail in FIG. 2 below.

To interface the robot control system 100 to a given type of robot 102, the robot interface 112 translates the commands and parameters generated by the feature/offset selector 110 to robot control information. For example and not to imply a limitation, a grappling robot arm may include a different command structure than a welding robot arm. Thus, the robot interface 112 translates parameters and commands from the feature/offset selector 110 to parameters and commands suitable for the particular type of robot 102.

The visual-servo controller 114 generates and/or acquires computer vision data (e.g., image(s) from a camera) and controls the servo motion of the robot 102. Optionally, the physical location and state of the robot may be sensed by appropriate sensors and that information used in the visual-servo controller 114. The visual-servo controller 114 enters a visual feedback loop, in which the visual-servo controller 114 identifies a tracking point via one or more images of the target object 103, moves the robot 102 toward the tracking point, and re-determines the position of the robot based on the relative location of the goal to the tracking point. To this end, the robot 102 provides status data to the visual-servo controller 114. The status data may include, for example, position information (e.g., the positions of each joint of the robot 102), velocity information, angular data, and/or other feedback data useful for operating a robot using visual-servo control. In some examples, the robot 102 and/or the visual-servo controller 114 includes sensors 116 to determine status data for the robot 102. The sensors 116 may include, for example, instruments to determine position information, velocity information, angular data, and/or other feedback data. The visual-servo controller 114 may use an offset from the tracking point to move the robot 102 to goal positions that are not easily tracked. When using the tracking point with the offset, the visual-servo controller 114 keeps the tracking point within its field of view and may further keep the tracking point within a certain portion of its field of view.

Additionally, the visual-servo controller 114 visually detects and generates one or more image(s) of the target object 103. The visual-servo controller 114 sends task data (e.g., the image(s) of the target object 103, the distance from the robot 102 to the target object 103) to the feature/offset selector 110. The feature/offset selector 110 receives the image(s) and determines several potential tracking points that the visual-servo controller 114 may be able to visually track. The feature/offset selector 110 then presents the image(s) of the target object 103 and the potential tracking points to the user 104 via the display 106. The user 104 determines which tracking point is, for example, most likely to remain constant as the feature/offset selector 110 emphasizes the potential tracking points. In some examples, the user 104 may cause the image to change (e.g., present a different angle view of the target object 103) if no acceptable tracking points are present in the image. When the feature/offset selector 110 emphasizes the tracking point selected by the user 104, the mental response of the user 104 is identified via the EEG system 108 and the feature/offset selector 110. In some examples, the feature/offset selector 110 presents the features and measures response of the user 104 multiple times to corroborate an identified selection. When the trackable feature is identified, the feature/offset selector 110 then presents an offset indicator and several directional indicators to the user 104 via the display 106, and the user 104 selects a position for the offset indicator via the EEG system 108 by selecting the directional indicators.

When the feature/offset selector 110 has determined the tracking point and the offset position relative to the tracking point, the feature/offset selector 110 sends the parameters and/or commands to the robot interface 112. The robot interface 112 translates the parameters and/or commands and provides the translated parameters and/or commands to the robot controller 114. The visual-servo controller 114 visually tracks the tracking point determined by the feature/offset selector 110, and then controls the robot 102 to effect the goal on the target object 103 at the offset to the tracking point determined by the feature/offset selector 110. As a result, the robot 102 effects the goal on the target object 103 at a position defined by the user 104 in a controlled and careful manner.

Figure 2:
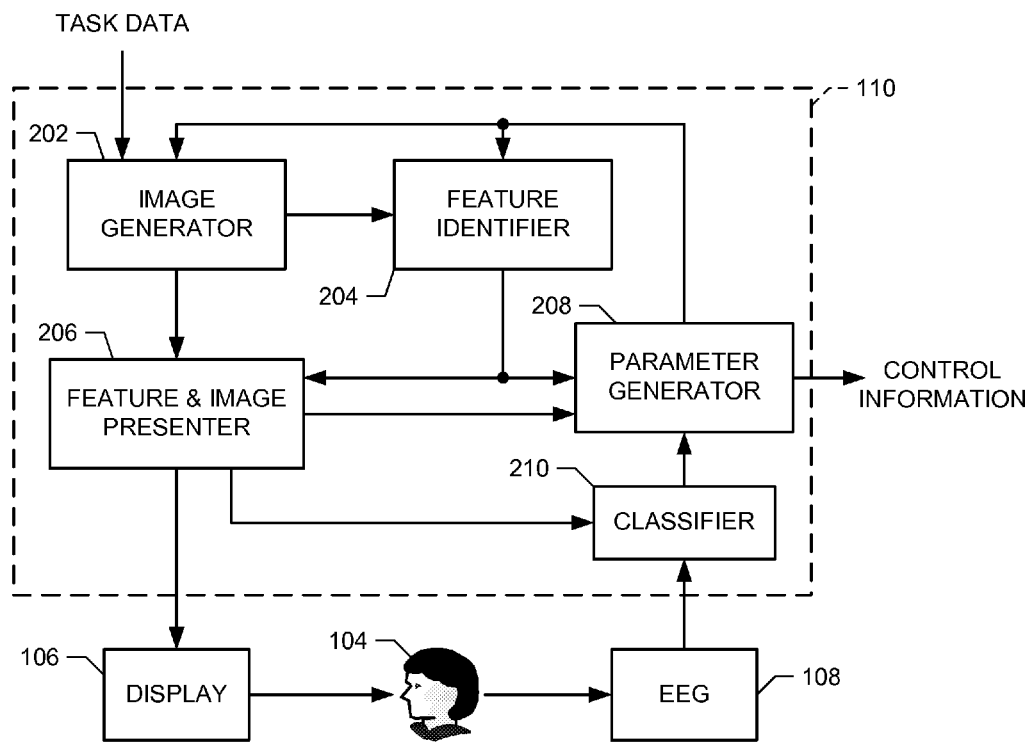
FIG. 2 is a more detailed block diagram of the feature/offset selector illustrated in FIG. 1.

FIG. 2 is a more detailed block diagram of the feature/offset selector 110 illustrated in FIG. 1. Generally, the feature/offset selector 110 receives task data (e.g., one or more images of the target object 103), provides an image of the target object 103 to a user 104 via the display 106, emphasizes features of the target object 103, and generates parameters to control the robot 102 based on the user's 104 selection. To this end, in one example implementation, the feature/offset selector 110 includes an image generator 202, a feature identifier 204, a feature and image presenter 206, a parameter generator 208, and a classifier 210. The EEG system 108 measures the user's 104 mental response to an emphasized feature, which is then classified by the classifier 210. The feature/offset selector 110 determines a goal or a constraint based on user 104 selection (via mental response) of an emphasized feature.

The image generator 202 receives the task data from the visual-servo controller 114 of FIG. 1. Based on the task data, the image generator 202 generates an image of the target object 103. The image serves as a reference image to the user 104. If the task data from the visual-servo controller 114 includes a three-dimensional model of the target object 102, the image generator 202 generates an image of one view of the target object 103. The user 104 may have the option to change the image if the image is inadequate.

The feature identifier 204 receives the object model and/or the image data from the image generator 202. Based on the object model and/or the image data, the feature identifier 204 determines one or more trackable features of the target object 103. A feature may refer to, for example, a particular portion of the image generated by the image generator 202, a particular portion of the target object 103 as determined from the object model, or, more generally, any individually-identifiable portion of an image or object. The features are overlaid on the image of the target object 103 for presentation to the user 104. As described below, features may be determined analytically. For example, the feature identifier 204 may determine that particular features of the image and/or model are particularly conducive to tracking. To this end, the feature identifier 204 may perform feature extraction, image segmentation, and/or volume segmentation on the target object 103 model.

The image and feature presenter 206 determines how the features are emphasized to the user 104 on the display 106. In some examples, the image and feature presenter 206 presents the target object 103 image or viewpoint in the background, and highlights one or more of the features to the user at a time. In other examples, the image and feature presenter 206 presents the target object 103 image or viewpoint in the background, and overlays markers at locations on the image corresponding to the features. The markers may be flashed one at a time, multiple markers may be flashed simultaneously, and/or the markers may all flash at different frequencies (from 5 Hz to 45 Hz). Depending on the method used to flash the markers or features, the classifier 210 will monitor for a different response from the EEG measurements from the EEG system 108 as described below. In some examples, the image and feature presenter 206 is implemented using rapid serial visual presentation (RSVP), which is available in the E-Prime® software package, a commercial stimulus presentation package sold by Psychology Software Tools, Inc.

While the image is displayed on the display 106, the user 104 focuses on a feature that is most appropriate (e.g., most reliable) for tracking by the visual-servo controller 114. As the image and feature presenter 206 emphasizes one of the features at a time on the display 106, the user 104 expects to see the feature as the EEG system 108 measures the mental responses of the user 104. If the image and feature presenter 206 emphasizes a feature not desired by the user 104, the classifier 210 does not detect a response from the measurements. However, if the image and feature presenter 206 emphasizes the feature desired by the user 104, the user's brain emits an electrical signal referred to as the P300 signal indicating recognition of the emphasized feature. The P300 signal response from the user 104 has approximately a 300 millisecond (ms) delay from the time the display 106 shows the emphasized feature. In this manner, the P300 signal acts as a "that's it!" signal indicating a match between the user's 104 desire and the emphasis of the same, which may be correlated by the parameter generator 208 and/or the classifier 210 to the emphasized tracking point or directional feature.

While the image and feature presenter 206 emphasizes features on the display 106 for the user 104, the image and feature presenter 206 also provides the emphasized feature information to the parameter generator 208. Thus, when the classifier 210 detects the P300 signal from the EEG measurement from the EEG system 108, the parameter generator 208 generates a goal parameter corresponding to the emphasized feature. After selection of the tracking feature, the parameter generator 208, the feature/offset selector 110 iterates to generate an offset marker and multiple directional features, to display and emphasize the marker and directional features to the user 104, detect a response to one or more emphasized directional features, and determine the offset relative to the tracking feature.

The classifier 210 detects a user response by correlating the brain wave measurements from the EEG system 108 with an external stimulus such as the emphasis of a feature to the user 104. In examples using a P300 response, there is approximately a 300 ms delay between display or highlighting of a given trackable feature and the corresponding mental response. In some examples multiple trackable features are displayed and/or highlighted within 300 ms and, thus, a mental response does not necessarily immediately follow the user-selected trackable feature. Thus, the classifier 210 may evaluate the user's mental response after highlighting all of the trackable features to determine which of the trackable features is most likely to have been selected by the user, and/or the classifier 210 may evaluate the user's mental response in real-time, taking into account the delay between highlighting of a given trackable feature and a corresponding mental response. When the response is detected, the classifier 210 provides an indication to the parameter generator 208 that the emphasized feature is the feature desired or selected by the user 104.

Figure 3:
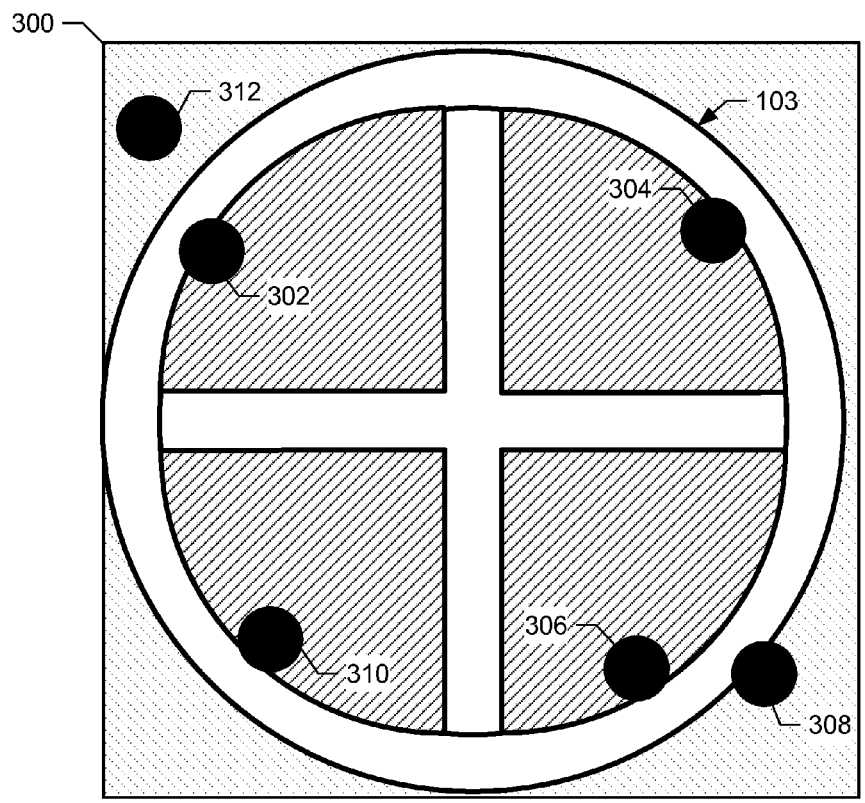
FIG. 3 is a diagram illustrating an image and several potential visual tracking features.

FIG. 3 is a diagram illustrating an image 300 and several potential visual tracking features 302-312. The example image 300 may be generated by the visual-servo controller 114, the image generator 202, and/or the feature identifier 204 of FIGS. 1 and 2. When the feature/offset selector 110 receives the image(s) from visual-servo controller 114, the image generator 202 generates the image 300 of the target object 103. In some examples, the image generator 202 only sends the image received from the visual-servo controller 114 to the feature and image presenter 206. The feature identifier 204 analyzes the image(s) to determine one or more potential trackable features in the image(s). One example algorithm that may be used to extract potential trackable features from the image(s) is the scale-invariant feature transform (SIFT) as described by David G. Lowe in "Distinctive Image Features from Scale-Invariant Keypoints," published in *International Journal of Computer Vision* 60(2): pp. 91-110, 2004. Multiple images may be useful for the feature identifier 204 to analyze whether any potential trackable features change in time. For example, if a potential trackable feature identified in one image is not present in a later image, the feature identifier 204 determines that the feature is not trackable.

The image generator 202 and the feature identifier 204 provide the images and the potential trackable features to the feature and image presenter 206. The feature and image presenter 206 then provides the image 300 and the potential trackable features 302-312 to the user 104 via the display 106. While displaying the image 300 and the potential trackable features 302-312, the feature and image presenter 206 emphasizes one of the features 302, 304, 306, 308, 310, or 312 at a time while the EEG system 108 measures the brain signal of the user 104. The image generator 202, 204, and 206 may update the image 300 over time to assist the user 104 in evaluating the potential trackable features 302-312. The user 104 analyzes the image(s) 300 using his or her knowledge and experience and concentrates on a desired trackable feature 302 that is likely to remain constant. The trackable feature 302 selected by the user 104 is preferably a feature 302 that will not move or disappear from the view of the visual-servo controller 114. When the classifier 210 identifies a mental response from the EEG measurements indicating that the user 104 has selected a trackable feature (e.g., the feature 302), the parameter generator 208 establishes the feature 302 as the tracking point for the visual-servo controller 114.

Figure 4:
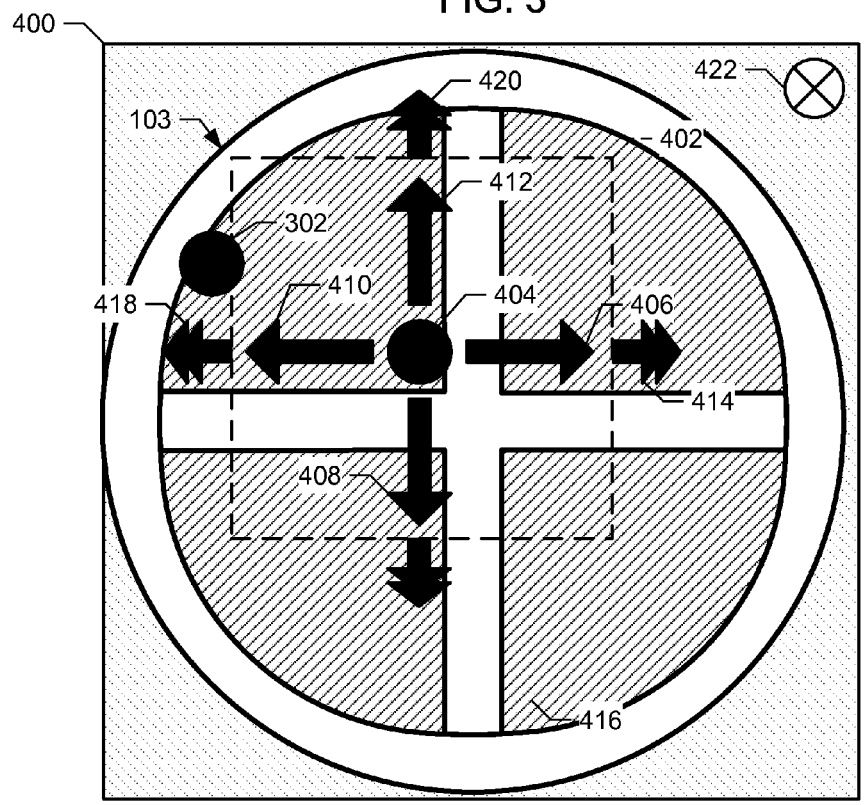
FIG. 4 is a diagram illustrating a selected visual tracking feature and an offset selector.

After selecting a tracking point, the feature/offset selector 110 determines the offset from the selected trackable feature 302 to the end goal. The location of the trackable feature 302 is not always the location of the end goal. FIG. 4 is a diagram illustrating a selected visual tracking feature 302 and an offset selector 402. The feature identifier 204 generates the offset selector 402, which includes an offset indicator 404 and several directional indicators 406, 408, 410, and 412. The feature and image presenter 206 then displays the image 300, the trackable feature 302, and the offset selector 402 to the user 104 via the display 106.

The user 104 selects the appropriate end goal position and uses the directional indicators 406-412 to move the offset indicator 404 to the end goal position. To this end, the feature and image presenter 206 emphasizes one of the directional indicators 406, 408, 410, or 412 at a time as the EEG system 108 measures the brain signals of the user 104. The user 104 concentrates on a particular directional indicator 406, 408, 410, or 412 corresponding to the desired direction. When the feature and image presenter 206 emphasizes the direction 406, 408, 410, or 412 desired by the user 104, the classifier 210 identifies a mental response from the EEG system 108 measurements and the parameter generator 208 determines that the emphasized directional indicator (e.g. 406) corresponds to the desired direction (e.g., right). The parameter generator 208 sends the direction to the feature identifier 204, which repositions the offset indicator 404 and the directional indicators 406-412 relative to the previous location.

The feature and image presenter 206 presents the image 300, and presents the offset indicator 404 and the directional indicators 406-412 in the new positions. The user 104 continues to select directional indicators 406-412 to incrementally move the offset indicator 404 to the desired position. When the offset indicator 404 is positioned correctly, the user 104 may select an accept feature 422 to indicate to the parameter generator 208 that the end goal location has been selected. The parameter generator 208 then transmits the parameters and commands to the robot interface 112, which translates the parameters and/or commands, if necessary, and sends the parameters and commands to the visual-servo controller 114.

In some examples, the feature and image presenter 206 presents only the left and right directional indicators 406 and 410 until the user 104 has positioned the offset indicator 404 at a particular left/right alignment. The feature and image presenter 206 then presents only the directional indicators 408 and 412, because the classifier 210 may have trouble identifying a mental response from a user 104 where the desired position lies in two directions (e.g., up and left, down and right).

Additionally or alternatively, the example feature identifier 204 may include additional directional indicators 414-420 to increase the speed of positioning. The directional indicators 406-412 may then be used for smaller incremental movement, and the directional indicators 414-420 are used for larger incremental movement.

Figure 5:
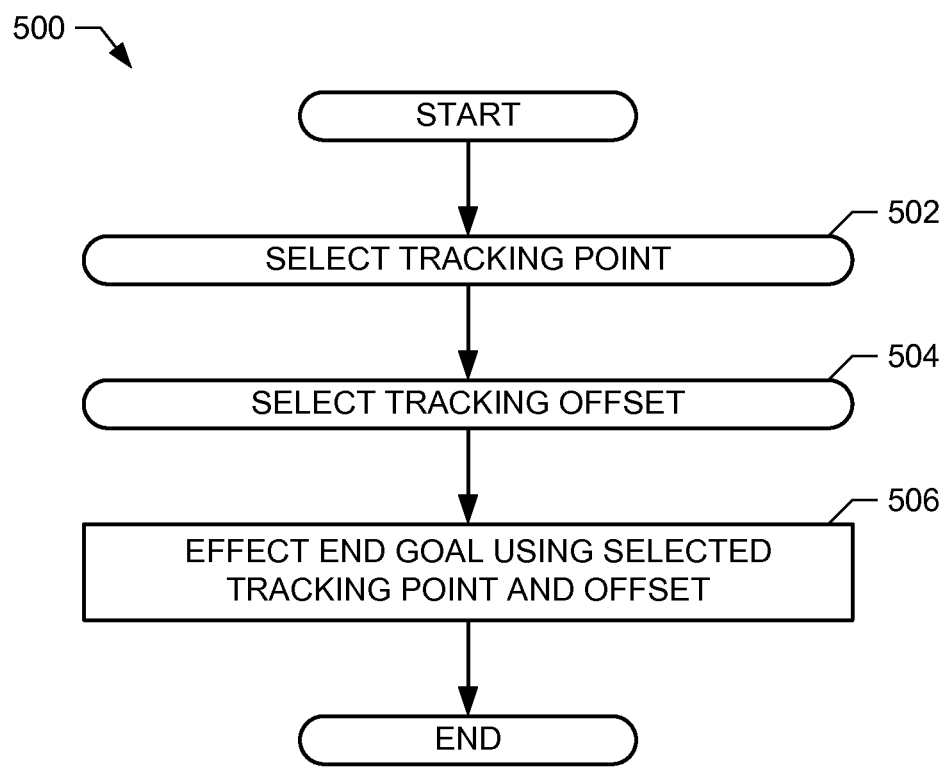
FIG. 5 is a flowchart representative of an example process that may be implemented to control a robot.
Figure 6:
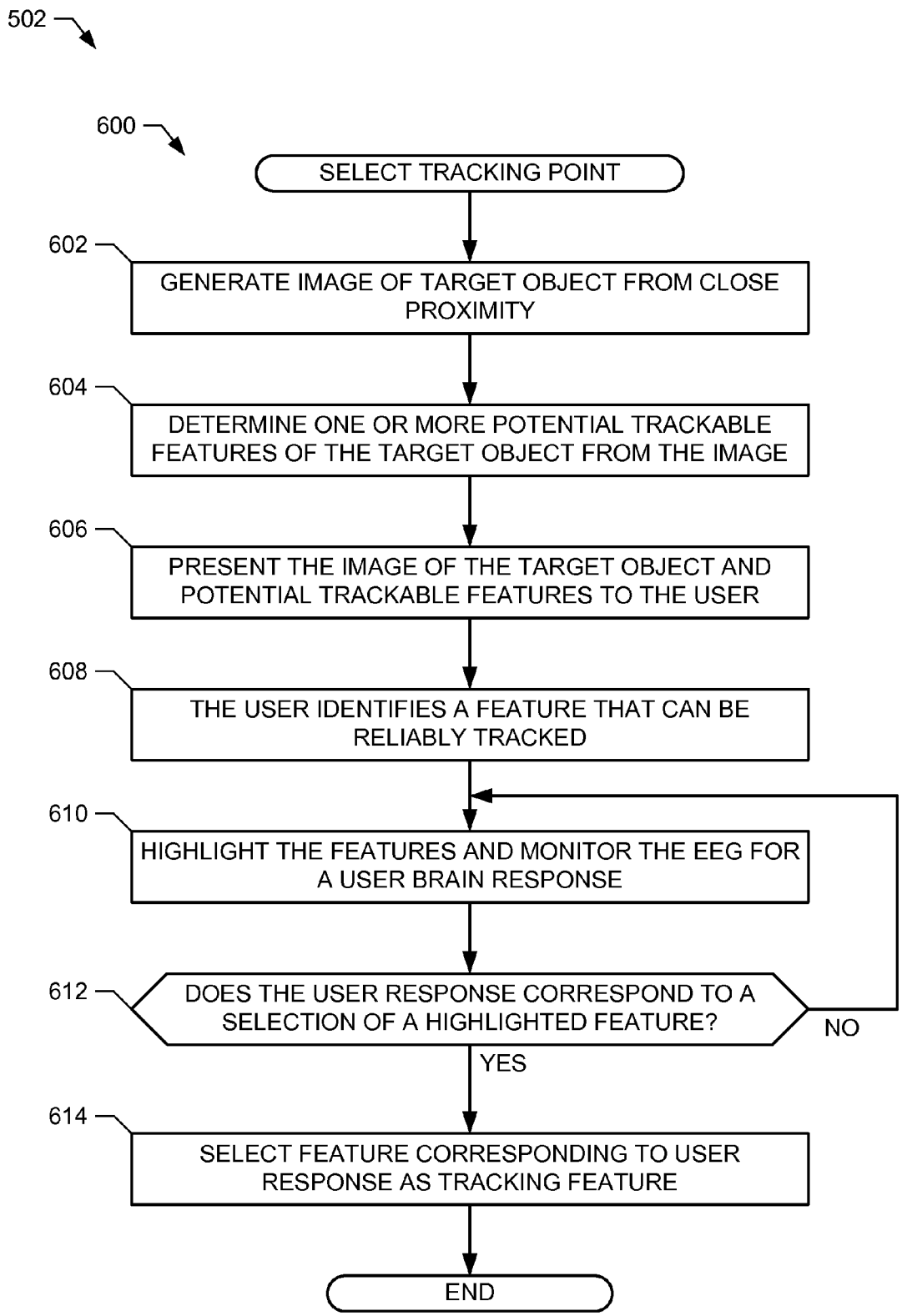
FIG. 6 is a flowchart representative of an example process that may be implemented to select a tracking point during near control.
Figure 7:
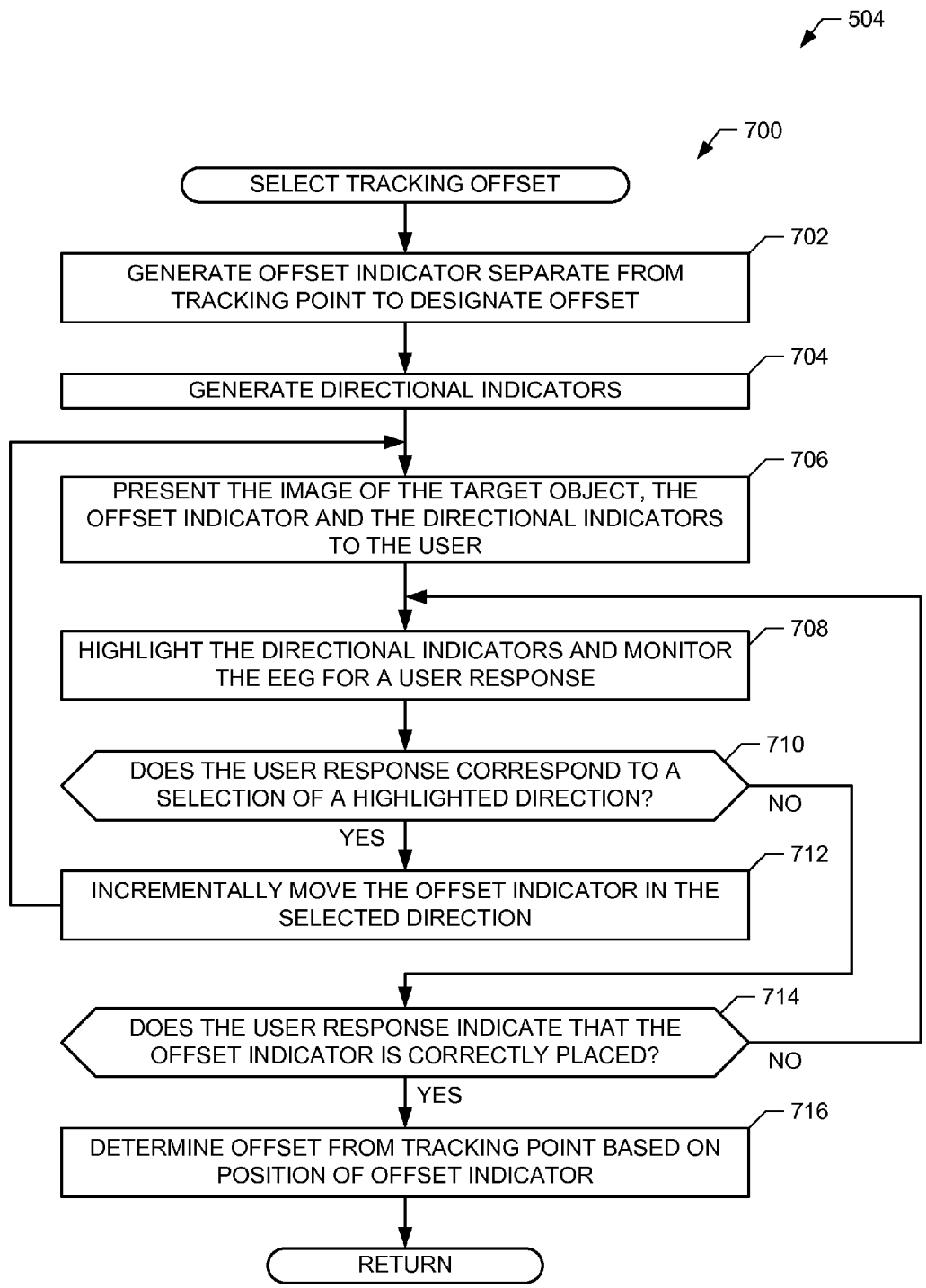
FIG. 7 is a flowchart representative of an example process that may be implemented to select a tracking offset from the tracking point.

While an example manner of implementing the robot control system 100 and the feature/offset selector 110 of FIGS. 1 and 2 is illustrated in FIGS. 5-7 below, one or more of the elements, processes and/or devices illustrated in FIGS. 1 and 2 may be combined, divided, re-arranged, omitted, eliminated and/or implemented in any other way. Further, the example display 106, the example EEG system 108, the example feature/offset selector 110, the example robot interface 112, the example visual-servo controller 114, the example image generator 202, the example feature identifier 204, the example feature and image presenter 206, the example parameter generator 208, the example classifier 210, and/or, more generally, the example robot control system 100 of FIGS. 1 and 2 may be implemented by hardware, software, firmware and/or any combination of hardware, software and/or firmware. Thus, for example, any of the display 106, the EEG system 108, the feature/offset selector 110, the robot interface 112, the visual-servo controller 114, the image generator 202, the feature identifier 204, the feature and image presenter 206, the parameter generator 208, the example classifier 210, and/or, more generally, the robot control system 100 of FIGS. 1 and 2 could be implemented by one or more circuit(s), programmable processor(s), application specific integrated circuit(s) (ASIC(s)), programmable logic device(s) (PLD(s)) and/or field programmable logic device(s) (FPLD(s)), etc.

When any of the appended system claims are read to cover a purely software and/or firmware implementation, at least one of the example display 106, the example EEG system 108, the example feature/offset selector 110, the example robot interface 112, the example visual-servo controller 114, the example image generator 202, the example feature identifier 204, the example feature and image presenter 206, the example parameter generator 208, the example classifier 210, and/or the example robot control system 100 are hereby expressly defined to include a tangible medium such as a memory, DVD, CD, etc. storing the software and/or firmware. Further still, the example robot control system 100 and/or the feature/offset generator 110 of FIGS. 1 and 2 may include one or more elements, processes and/or devices in addition to, or instead of, those illustrated in FIGS. 1 and 2, and/or may include more than one of any or all of the illustrated elements, processes and devices.

FIG. 5 is a flowchart representative of an example process 500 that may be implemented using machine readable instructions executed by a processor to control a robot. The example process may be performed by, for example, the robot system 100 of FIG. 1 to effect an end goal. The example process 500 begins by selecting a tracking point (block 502). The tracking point may be selected using the process 502 described with reference to FIG. 6 below. The process 500 then selects an offset from the tracking point to the end goal (block 504). When the tracking point and the offset from the tracking point have been selected, the example process 500 effects the end goal at the goal point using the selected tracking point and the selected offset (block 506). By tracking the selected tracking point, the process 500 effects the end goal via the robot 102 of FIG. 1 at a position selected as the offset from the tracking point. When the robot 102 has effected the end goal (block 506), the example process 500 may end.

FIG. 6 is a flowchart representative of an example process 600 that may be implemented using machine readable instructions executed by a processor to select a tracking point. The process 600 may be used to implement block 502 of the example process 500 illustrated in FIG. 5. The example process 502 begins by generating an image (e.g., the image 300 of FIG. 3, via the visual-servo controller 114 and/or the image generator 202) of the target object 103 (block 602). The image 300 may be, for example, one or more camera images. Based on the image 300, the feature identifier 204 determines one or more potential trackable features 302-312 of the target object 103 (block 604). The feature and image presenter 206 presents the image 300 and the potential trackable features 302-312 to the user 104 (block 606). The user 104 identifies a feature (e.g., 302) that can be reliably tracked (block 608).

The feature and image presenter 206 then highlights each of the trackable features (e.g., 302) and the classifier 210 monitors the EEG system 108 for a mental response from the user 104 (block 610). In some examples, block 610 may be performed using RSVP by rapidly presenting a number of images to the user 104 while the classifier monitors the EEG system 108 for a mental response from the user 104. If the user's mental response corresponds to a selection of one of the highlighted trackable features (block 612), the parameter generator 208 selects the feature 302 corresponding to the user response as the tracking feature (block 614). However, if the user's 104 mental response does not correspond to a selection of the highlighted feature 302 (block 612), control returns to block 610 to highlight another of the potential trackable features 304-312. When the parameter generator 208 has selected a tracking feature (block 614), the example process 502 may end and control returns to block 504 of FIG. 5.

FIG. 7 is a flowchart representative of an example process 700 that may be implemented using machine readable instructions executed by a processor to select a tracking offset from the tracking point. The process 700 may be used to implement block 504 of the example process 500 illustrated in FIG. 5. To select a tracking offset, the example feature identifier 204 generates an offset indicator (e.g., the offset indicator 404) separate from the tracking point 302 to designate the location of the offset (block 702). The feature identifier 204 further generates directional indicators (e.g., the directional indicators 406-412 and/or 414-420) (block 704).

The feature and image presenter 206 presents the image 300, the offset indicator 404 and the directional indicators 404-412 to the user 104. The feature and image presenter 206 then highlights each of the directional indicators and the classifier 210 monitors the mental response of the user 104 via EEG system 108 measurements (block 708). If the classifier 210 determines (e.g., via highlighting the directional indicators and monitoring the measurements from the EEG system 108) that the mental response of the user 104 corresponds to a selection of one of the highlighted directions (e.g., 406, right) (block 710), the parameter generator 208 instructs the feature identifier 204 to move the offset indicator 404 incrementally in the selected direction (e.g., to the right) (block 712). After moving the offset indicator 404 (block 712), control returns to block 706 to redisplay the target object 103, the offset indicator 404, and the directional indicators 404-412.

If the classifier 210 detects that the user's 104 mental response to highlighting the directional indicators 406 does not correspond to a selection (block 710), the parameter generator 208 determines whether the response indicates that the user's 104 response indicates that the offset indicator 404 is correctly placed (block 714). If the offset indicator 404 is not correctly placed (block 714), control returns to block 708 to highlight the directional indicators (e.g., 408). However, if the parameter generator 208 determines that the user's 104 response indicates that the offset indicator 404 is correctly placed (block 714), the parameter generator 208 determines the offset from the tracking point 302 based on the position of the offset indicator (block 716). The example process 504 may then end, and control returns to block 506 of FIG. 5 to effect the end goal.

The example processes 500, 600, and 700 described above use an EEG system to detect a P300 brain signal by emphasizing one feature at a time. Additionally or alternatively, the example processes may use an EEG system to detect a steady-state visual evoked potential (SSVEP) to allow the user to select a feature, robot configuration, or tracking point. Using an SSVEP, the feature/offset selector 110 of FIG. 1 (via the display 106) displays multiple features or markers and flickers each feature or marker at a different rate between 5 Hz and 45 Hz. When the user gazes on a desired feature or marker, the EEG detects a particular SSVEP corresponding to the particular feature or marker. The parameter generator 208 then selects the feature or marker corresponding to the frequency evoking the SSVEP.

While the P300 evoked response provides a strong and readily detected signal, training may be required to calibrate or train the classifier 210 to a user's brain activity. During an example training procedure, approximately 250 images are shown to the user in a span of 30 seconds while the user selects predetermined images and the classifier 210 monitors the EEG system 108 to learn about the user's mental responses. The user may instruct the classifier 210 (e.g., via a button) when the classifier 210 is incorrect. Other types of measurements may require different training techniques. Some examples of training techniques that may be used are described in "Cortically-coupled computer vision for rapid image search," by Gerson, et al., published in *IEEE Transactions on Neural Systems and Rehabilitation Engineering*, [see also *IEEE Trans. on Rehabilitation Engineering*], Vol. 14, No. 2. (2006), pp. 174-179.

Figure 8:
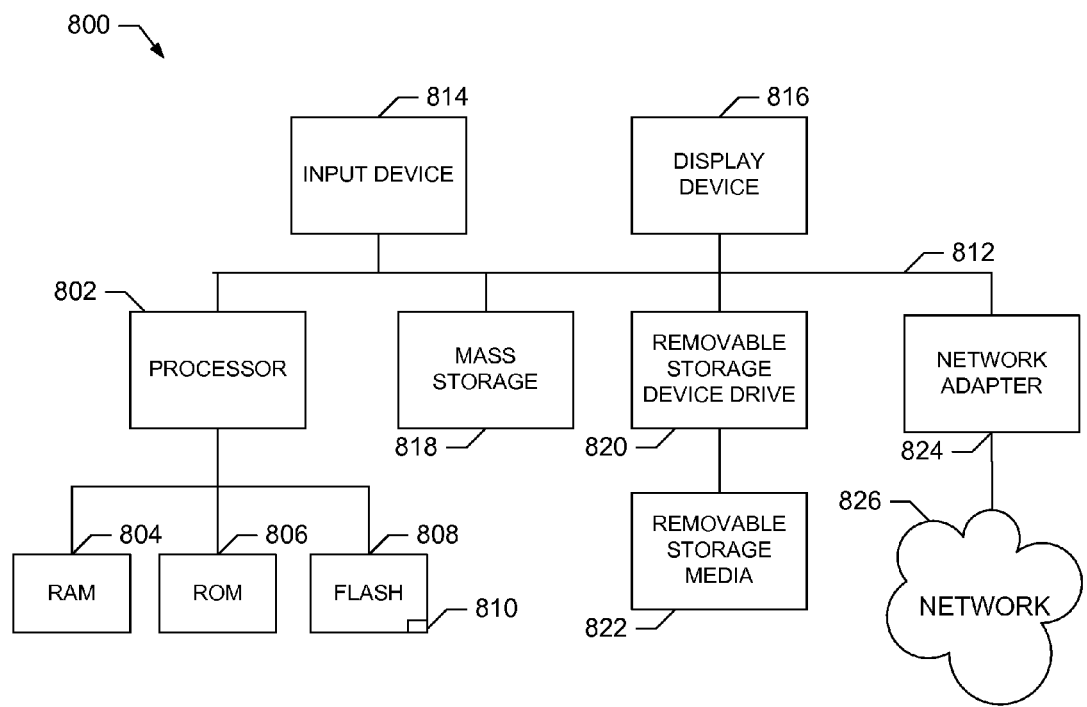
FIG. 8 is a diagram of an example processor system that may be used to implement the example systems and methods described herein.

FIG. 8 is a diagram of an example processor system 800 that may be used to implement the example processes 500, 502, and 504 described herein, as well as the example display 106, the example EEG system 108, the example feature/offset selector 110, the example robot interface 112, the example visual-servo controller 114, the example image generator 202, the example feature identifier 204, the example feature and image presenter 206, the example parameter generator 208, the example classifier 210, and/or, more generally, the example robot control system 100 of FIGS. 1 and 2.

Turning now to FIG. 8, an example processor system 800 includes a processor 802 having associated memories, such as a random access memory (RAM) 804, a read only memory (ROM) 806 and a flash memory 808. The RAM 804, the ROM 806, and/or the flash memory 808 may store machine-readable instructions that implement the processes 500, 502, and/or 504 of FIGS. 5, 6, and 7. The flash memory 808 of the illustrated example includes a boot block 810. The processor 802 is coupled to an interface, such as a bus 812 to which other components may be interfaced. In the illustrated example, the components interfaced to the bus 812 include an input device 814, a display device 816, a mass storage device 818 and a removable storage device drive 820. The removable storage device drive 820 may include associated removable storage media 822 such as magnetic or optical media.

The example processor system 800 may be, for example, a conventional desktop personal computer, a notebook computer, a workstation or any other computing device. The processor 802 may be any type of processing unit, such as a microprocessor from the Intel® Pentium® family of microprocessors, the Intel® Itanium® family of microprocessors, and/or the Intel XScale® family of processors. The memories 804, 806 and 808 that are coupled to the processor 802 may be any suitable memory devices and may be sized to fit the storage demands of the system 800. In particular, the flash memory 808 may be a non-volatile memory that is accessed and erased on a block-by-block basis.

The input device 814 may be implemented using a brain monitoring system such as an EEG system (e.g., the EEG system 108 of FIGS. 1 and 2), including an amplifier, a cap or other wearable device including a plurality of electrodes that may be worn by a user of the processing system 800, and a data collection device, and/or any one or more of a keyboard, a mouse, a touch screen, a track pad, a barcode scanner or any other device that enables a user to provide information to the processor 802.

The display device 816 may be, for example, a liquid crystal display (LCD) monitor, a cathode ray tube (CRT) monitor or any other suitable device that acts as an interface between the processor 802 and a user. The display device 816 as pictured in FIG. 8 includes any additional hardware required to interface a display screen to the processor 802.

The mass storage device 818 may be, for example, a conventional hard drive or any other magnetic or optical media that is readable by the processor 802.

The removable storage device drive 820 may, for example, be an optical drive, such as a compact disk-recordable (CD-R) drive, a compact disk-rewritable (CD-RW) drive, a digital versatile disk (DVD) drive or any other optical drive. It may alternatively be, for example, a magnetic media drive. The removable storage media 822 is complimentary to the removable storage device drive 820, inasmuch as the media 822 is selected to operate with the drive 820. For example, if the removable storage device drive 820 is an optical drive, the removable storage media 822 may be a CD-R disk, a CD-RW disk, a DVD disk or any other suitable optical disk. On the other hand, if the removable storage device drive 820 is a magnetic media device, the removable storage media 822 may be, for example, a diskette or any other suitable magnetic storage media.

Although this patent discloses example systems including software or firmware executed on hardware, it should be noted that such systems are merely illustrative and should not be considered as limiting. For example, it is contemplated that any or all of these hardware and software components could be embodied exclusively in hardware, exclusively in software, exclusively in firmware or in any combination of hardware, firmware and/or software. Accordingly, while the above specification described example systems, methods, apparatus, and articles of manufacture, the examples are not the only way to implement such systems, methods, apparatus, and articles of manufacture. While the foregoing describes example processes, the processes may be also implemented as computer-readable instructions encoded onto a machine-accessible medium. Therefore, although certain example systems, methods, apparatus, and articles of manufacture have been described herein, the scope of coverage of this patent is not limited thereto. On the contrary, this patent covers all systems, methods, apparatus and articles of manufacture fairly falling within the scope of the appended claims either literally or under the doctrine of equivalents.

What is claimed is:

1. A method to control a robot, comprising:
   presenting one or more potential trackable features of an object to be contacted by the robot;
   emphasizing at least one of the potential trackable features;
   determining, using a processor, a selection of one of the emphasized features as a tracking point by monitoring a first mental response to emphasizing the feature; and
   effecting an end goal, at a position based on the selected feature, via the robot by tracking the selected feature during the effecting.

2. A method as defined in claim 1, wherein monitoring the first mental response comprises:
   monitoring an electroencephalogram (EEG) to identify a brain signal, wherein the brain signal corresponds to the selection of the potential trackable feature; and
   associating the selected potential trackable feature as the tracking point corresponding to the brain signal.

3. A method as defined in claim 1, further comprising:
   presenting the object and the selected feature;
   presenting an offset indicator and one or more directional indicators;
   emphasizing at least one of the directional indicators and monitoring an EEG for a second mental response corresponding to a selection of the emphasized directional indicator; and
   moving the offset indicator in a direction corresponding to a first one of the emphasized directional indicators in response to identifying the second mental response from the EEG as corresponding to a selection of the first emphasized directional indicator.

4. A method as defined in claim 3, wherein emphasizing the potential trackable feature or the directional indicator comprises at least one of flashing, blinking or flickering the potential trackable feature or the directional indicator.

5. A method as defined in claim 1, further comprising determining potential trackable features by analyzing a plurality of images of the object to determine features that are consistently present.

6. A method as defined in claim 1, wherein effecting the end goal comprises using a visual-servo controller to track the selected feature and to servo a robot based on the tracking.

7. A method as defined in claim 1, wherein effecting the end goal comprises controlling a robotic grappling task to grapple the object at the end goal.

8. A tangible machine readable storage medium comprising machine readable instructions which, when executed, cause a machine to at least:
   present one or more potential trackable features of an object to be contacted by a robot;
   emphasize at least one of the potential trackable features;
   determine a selection of one of the emphasized features as a tracking point by monitoring a first mental response to emphasizing the feature; and
   effect an end goal, at a position based on the selected feature, via the robot by tracking the selected feature during the effecting.

9. An article of manufacture as defined in claim 8, wherein monitoring the first mental response comprises:
   monitoring an electroencephalogram (EEG) to identify a brain signal, wherein the brain signal corresponds to the selection of the potential trackable feature; and
   associating the selected potential trackable feature as the tracking point corresponding to the brain signal.

10. An article of manufacture as defined in claim 8, wherein the first mental response comprises at least one of a P300 signal or a steady-state visual evoked response.

11. An article of manufacture as defined in claim 8, wherein the instructions, when executed, further cause the machine to:
present the object and the selected feature;
present an offset indicator and one or more directional indicators;
emphasize at least one of the directional indicators and monitor an EEG for a second mental response corresponding to a selection of the emphasized directional indicator; and
move the offset indicator in a direction corresponding to a first one of the emphasized directional indicators in response to identifying the second mental response from the EEG as corresponding to a selection of the first emphasized directional indicator.

12. An article of manufacture as defined in claim 8, wherein the instructions, when executed, further cause the machine to generate an image of the object and analyze the image to determine the potential trackable features.

13. An article of manufacture as defined in claim 8, wherein the instructions, when executed, further cause the machine to determine potential trackable features by analyzing a plurality of images of the object to determine features that are consistently present.

14. An apparatus, comprising:
a processor; and
a memory storing computer readable instructions which, when executed by the processor, cause the processor to:
present one or more potential trackable features of an object to be contacted by a robot;
emphasize at least one of the potential trackable features;
determine a selection of one of the emphasized features as a tracking point by monitoring a first mental response to emphasizing the feature; and
effect an end goal, at a position based on the selected feature, via the robot by tracking the selected feature during the effecting.

* * * * *